US009623230B2

(12) United States Patent
Kim et al.

(10) Patent No.: US 9,623,230 B2
(45) Date of Patent: Apr. 18, 2017

(54) IV FLOW CONTROLLER HAVING FLUSHING FEATURE

(71) Applicants: Dong Kwan Kim, Gyeonggi-do (KR); Dong Sik Kim, Seoul (KR)

(72) Inventors: Dong Kwan Kim, Gyeonggi-do (KR); Dong Sik Kim, Seoul (KR)

( * ) Notice: Subject to any disclaimer, the term of this patent is extended or adjusted under 35 U.S.C. 154(b) by 299 days.

(21) Appl. No.: 14/409,843

(22) PCT Filed: Nov. 8, 2012

(86) PCT No.: PCT/KR2012/009358
§ 371 (c)(1),
(2) Date: Dec. 19, 2014

(87) PCT Pub. No.: WO2013/191335
PCT Pub. Date: Dec. 27, 2013

(65) Prior Publication Data
US 2015/0190628 A1    Jul. 9, 2015

(30) Foreign Application Priority Data
Jun. 20, 2012   (KR) .......................... 10-2012-0065986

(51) Int. Cl.
*A61M 5/00* (2006.01)
*A61M 39/28* (2006.01)
*A61M 39/00* (2006.01)

(52) U.S. Cl.
CPC .......... *A61M 39/28* (2013.01); *A61M 39/286* (2013.01); *A61M 2039/0018* (2013.01)

(58) Field of Classification Search
CPC .......... A61M 2039/0018; A61M 39/28; A61M 39/286; A61M 1/0078; A61M 39/284; A61M 5/16881
See application file for complete search history.

(56) References Cited

U.S. PATENT DOCUMENTS 2,595,511 A * 5/1952 Butler ................. A61M 39/286
  251/6
3,960,149 A * 6/1976 Bujan ................... A61M 39/28
  24/115 L (Continued)

FOREIGN PATENT DOCUMENTS

| KR | 1020040088407 | 10/2004 |
| KR | 100909342 | 7/2009 |
| KR | 101024406 | 3/2011 |

*Primary Examiner* — Rebecca E Eisenberg
(74) *Attorney, Agent, or Firm* — Roberts Mlotkowski Safran Cole and Calderon P.C.

(57) ABSTRACT

Provided is an IV flow controller which adjusts the amount of an IV material supplied to a patient through an IV tube and to which a flushing feature is added. The IV controller according to the present invention includes: a first body unit, a second body unit, a fixed roller, and a driving roller. The fixed roller is fixedly and rotatably arranged, and has a first gear unit and a second gear unit. The driving roller is accommodated such that a portion thereof is exposed, and the driving roller is moved along the lengthwise direction while controlling the flow of the IV when the exposed portion is turned. Also, in the flushing position, the driving roller rotates in cooperation with the first gear unit of the fixed roller across the IV tube so as to flush the latter. The second gear unit of the fixed roller may be configured so as to have a ratchet gear, and the second body unit has a pawl which meshes with the ratchet gear of the fixed roller in order to prevent reverse rotation. According to the present invention, flushing in the reverse direction is prevented by the ratchet gear, and thus medical accidents caused by reverse flushing can be prevented.

10 Claims, 9 Drawing Sheets

(56) References Cited

U.S. PATENT DOCUMENTS

| | | | | |
|---|---|---|---|---|
| 4,285,492 A | * | 8/1981 | Bujan | A61M 39/286 251/6 |
| 4,335,866 A | * | 6/1982 | Bujan | A61M 39/286 251/6 |
| 4,911,399 A | * | 3/1990 | Green | A61M 39/285 251/4 |
| 5,259,587 A | * | 11/1993 | D'Alessio | A61M 39/285 251/297 |
| 5,318,546 A | * | 6/1994 | Bierman | A61M 39/284 128/898 |
| 5,827,238 A | * | 10/1998 | Kelley | A61M 39/286 285/314 |
| 6,168,577 B1 | * | 1/2001 | Niederjohn | A61M 3/0279 604/23 |
| 8,221,388 B2 | * | 7/2012 | Swisher | A61M 39/28 604/530 |
| 2003/0175609 A1 | * | 9/2003 | Combes | G03G 9/0804 430/108.22 |
| 2007/0272886 A1 | * | 11/2007 | Abe | A61M 39/286 251/6 |
| 2009/0247964 A1 | * | 10/2009 | Kitani | A61M 39/28 604/250 |
| 2009/0312719 A1 | | 12/2009 | Chew | |
| 2012/0119121 A1 | * | 5/2012 | Hopf | A61M 39/285 251/4 |

\* cited by examiner

IV FLOW CONTROLLER HAVING FLUSHING FEATURE

CROSS-REFERENCE TO RELATED APPLICATIONS

This is a US national phase of PCT patent Application No. PCT/KR2012/009358 having an International filing date of Nov. 8, 2012, which claims priority to Korean Patent Application No. 10-2012-0065986, filed on Jun. 20, 2012, the entireties of which are incorporated herein by reference.

FIELD OF THE INVENTION

The present invention relates to an IV(Intravenous) flow controller having a flushing feature, and in particular to an IV flow controller wherein flushing function is added to an IV flow controller configured to control the amount of IV flow which is supplied through an IV flow tube to a patient.

BACKGROUND OF THE INVENTION

An IV flow controller in general is used so as to adjust the rate of IV flow when supplying a Ringer solution of the IV. The IV flow may decrease or the supply of the IV may be stopped if a patient makes a motion or moves. In case where a medicine is administrated through an IV flow tube, it may need to normalize the supply of the IV before a patient enters a surgical operation zone or in the middle of the surgical operation.

The action where the supply of the IV flow is normalized with the aid of the IV flow tube is called a flushing.

For the sake of the supply and flushing of the IV, an injector adapter with three branches in a Y-shape has been conventionally used. An IV flow tube (Ringer tube) is inserted into both sides of each of two branches among three branches, and a rubber member is inserted inside of the remaining one branch. In this configuration, an injection needle is penetrated into the rubber member, and then an injection medicine is withdrawn into the IV flow tube. However, such a configuration may cause an accident where an injector needle may hurt a user because the injection is performed by penetrating the injection needle into the rubber member. Since the use of an injector is common, an ordinary person may have a problem when the IV is used.

The U.S. Pat. No. 6,953,450 describes a configuration characterized in that the injection needle is not used; however the configuration is complicated, and the price is high, and there still are an inconvenience and a problem for an ordinary person to use.

A device configured to perform a flushing function with the aid of an electronic unit is disclosed, but it is expensive, and it is hard for an ordinary person to use.

In order to improve the above-mentioned problems, the inventor of the present application filed the Korean Patent Registration No. 10-1024406. The Korean Patent Registration No. 10-1024406 includes a first body unit, a second body unit, a fixed roller and a driving roller. The first body unit includes a bottom surface part and a wall surface part, with an open space being formed at the opposite side of the wall surface part. The second body unit is secured to the first body unit, and a space through which an IV flow tube passes is formed in a longitudinal direction between the second body unit and the first body unit. The fixed roller is fixedly installed and is rotatable against the first body unit and the second body unit, and the driving roller is accommodated in such a way that part of the driving roller is exposed to the open space between the first body unit and the second body unit. When the exposed portion is rotated, it moves along the longitudinal directions of the first body unit and the second body unit. During this operation, the degree where the IV flow tube is pressed against the wall surface part varies for thereby regulating the rate of IV flow. In a state where the driving roller is positioned at an end portion of one side, the driving roller rotates in cooperation with the fixed roller in a state where the IV flow tube is disposed between them, for thereby performing a flushing function.

In the above-described IV flow controller having such a configuration, when the IV flow controller is pushed up in a state where the driving roller is at the flushing position, the IV solution may flow in the reverse direction. In addition, the pressure may excessively increase due to the excessive flushing operation.

DETAILED DESCRIPTION OF THE INVENTION

Accordingly, the present invention is made in an effort to resolve the above-mentioned problems It is an object of the present invention to provide an IV flow controller having a flushing feature. It is another object of the present invention to provide an IV flow controller which is capable of preventing the flushing operation from being performed in the reverse direction. It is further another object of the present invention to provide an IV flow controller which makes it possible to prevent an excessive flushing operation.

To achieve the above objects, there is provided an IV flow controller which includes a first body unit, a second body unit, a fixed roller and a driving roller. The first body unit includes a bottom surface unit and a wall surface unit and an open space at the opposite side of the wall surface unit and also includes a tube pressing surface and a fixed roller groove. The second body unit is secured to the first body unit and forms a space through which the IV flow tube passes, in the longitudinal direction between the second body unit and the first body unit and includes a tube pressing surface and a fixed roller groove. The fixed roller is rotatably fixed since the shaft is inserted into the fixed roller groove of each of the first body unit and the second body unit and includes a first gear unit and a second gear unit. The driving roller is accommodated in such a way that part of the driving roller is exposed toward the open space between the first body unit and the second body unit, and when the exposed portion is rotated, the degree where the IV flow tube is pressed against the tube pressing surface while moving along the longitudinal direction of each of the first body unit and the second body unit varies, for thereby regulating the flow of IV solution. The flushing is performed since it rotates in cooperation with the first gear unit of the fixed roller with an IV flow tubing being interposed at the flushing position of one end portion of one side moving along the longitudinal direction.

The second gear unit of the fixed roller may be formed of a latchet gear, and the second body unit includes a pawl which is engaged with the latchet gear of the fixed roller and is configured to prevent reverse rotation.

A first driving roller guide groove is formed at the bottom surface part of the first body unit so as to accommodate an end portion of one side of the shaft of the driving roller and to guide the driving roller in the longitudinal direction, and a second driving roller guide groove is formed at a portion corresponding to the first driving roller guide groove of the second body unit so as to guide the driving roller in the longitudinal direction.

At least a part of the tube pressing surface is formed of a slanted surface, and the average distance between the tube pressing surface and the driving roller guide groove gradually varies while the driving roller moves along the longitudinal direction.

Since an escape groove is formed toward the open space and near an end portion of one side moving along the longitudinal direction at each of the first driving roller guide groove and the second driving roller guide groove, when the driving roller enters into the escape groove, the pressing of the IV flow tube between the driving roller and the wall surface unit is minimized.

In addition, a flushing escape groove is formed at each of the first and second driving roller guide grooves of the flushing position, and a tube pressing surface is formed at the distance where the IV solution does not flow through the IV flow tube since the driving roller maximally presses the IV flow tube at the IV flow-blocking position at the end portion of the opposite side of the flushing position. A protrusion for providing a snapping-like feeling may be formed at each of the first and second driving roller guide grooves near the IV flow-blocking position.

The IV flow controller may include two leg units at each of which an engaging hook is formed inside, and a clip including two handle units. A clip accommodation groove may be formed at an outer surface of each of the first body unit and the second body unit so as to accommodate the clip. A slit in which the engaging hook is inserted and movable, is formed at the clip accommodation groove.

A groove is formed at one side of the handle unit of the clip, and a protrusion which is inserted into the groove is formed at the other side for thereby fixing the clip at the IV flow tube.

Advantageous Effects

The IV flow controller of the present invention includes a simple structure formed of a first body unit, a second body unit, a fixed roller and a driving roller, so the manufacturing cost is low, and it does not need to use an injector for the sake of a flushing function, so any infection may be prevented, and an ordinary person may use conveniently. In addition, any medical accident due to a reverse operation of flushing may be prevented since the flushing operation in the reverse direction may be prevented using a latchet gear. In addition, a predetermined rotation noise generates between the latchet gear and a pawl during the flushing operation, so a user may have awareness with respect to the excessive flushing operation. In addition, any excessive flushing operation may be physically prevented by installing a clip.

MODE FOR INVENTION

The exemplary embodiments of the IV flow controller according to the present invention will be described with reference to the accompanying drawings.

Figure 1:
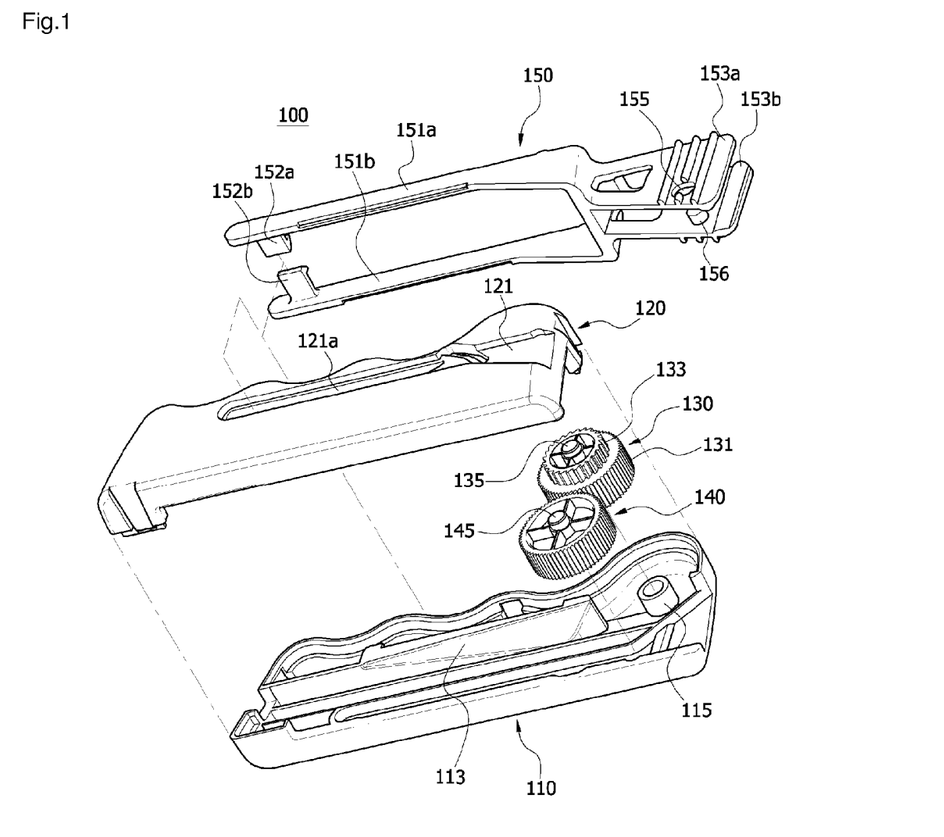
FIG. 1 is a disassembled perspective view illustrating an IV flow controller according to an exemplary embodiment of the present invention.
Figure 2:
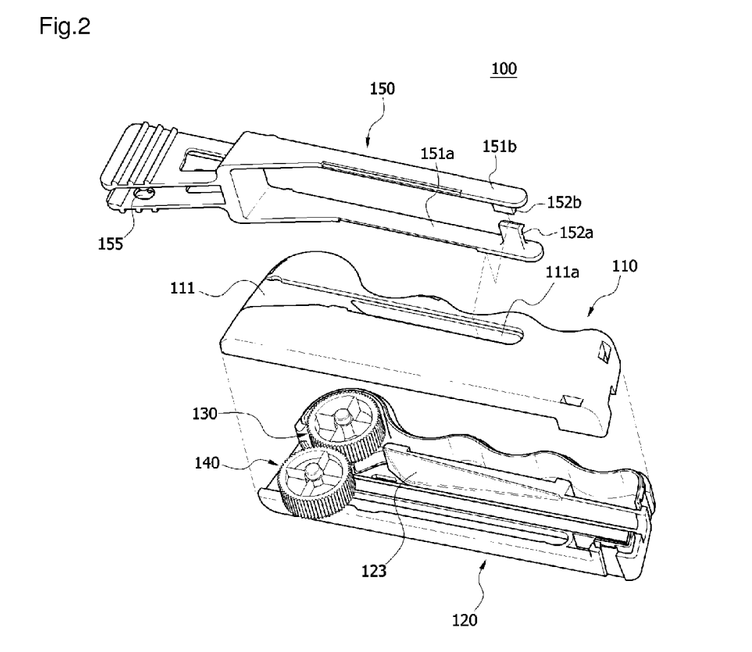
FIG. 2 is a disassembled perspective view illustrating an IV flow controller when viewing from another direction according to an exemplary embodiment of the present invention.
Figure 3:
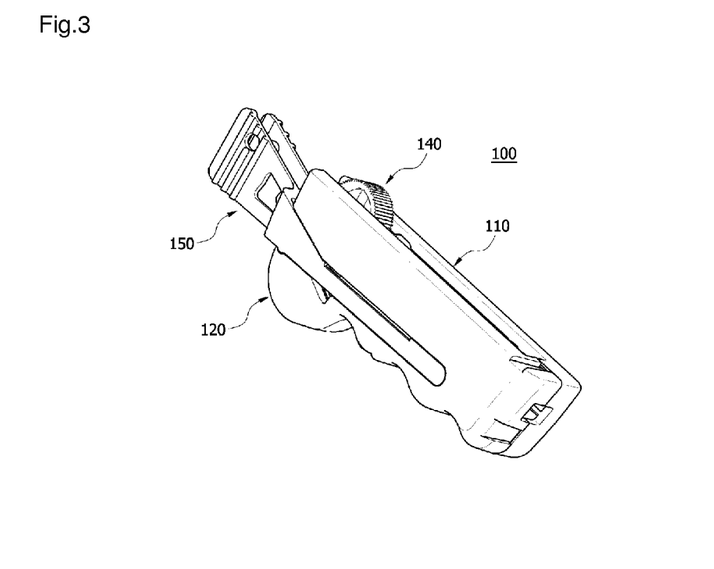
FIG. 3 is a perspective view illustrating an exterior of an IV flow controller according to the present invention.
Figure 4:
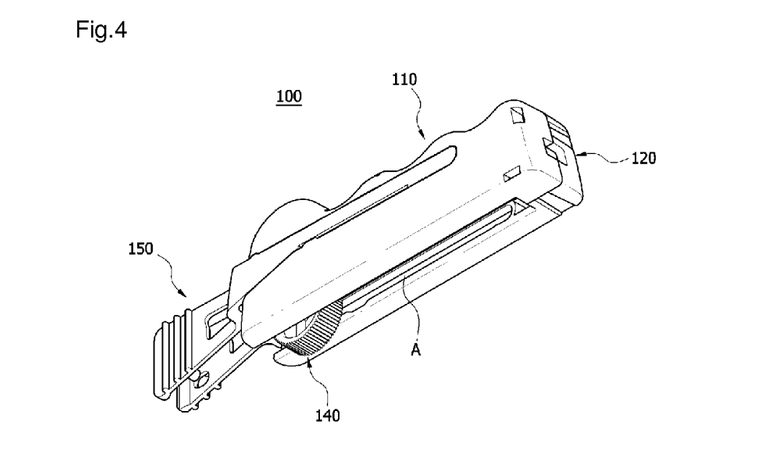
FIG. 4 is a perspective view illustrating an exterior of an IV flow controller when viewing from another direction according to the present invention.

FIGS. 1 and 2 are disassembled perspective views illustrating an IV flow controller according to an exemplary embodiment of the present invention, and FIGS. 3 and 4 are perspective views illustrating an exterior of an IV flow controller according to the present invention.

The IV flow controller 100 according to the present invention includes a first body unit 110, a second body unit 120, a fixed roller 130, and a driving roller 140. There is further provided a clip 150 which is assembled to clip accommodation grooves 111 and 121 of the first body unit 110 and the second body unit 120.

The first body unit 110 includes a bottom surface part, and a wall surface part is formed at one end of one side of the bottom surface part. At least a part of the opposite side of the wall surface part is open. In the wall surface part, grooves may be formed where user's fingers contact in order to grab easily with hands.

The second body unit 120 is engaged to the first body unit 110 and forms a space through which an IV flow tube passes in the longitudinal direction between the first body unit 110 and the second body unit 120. The second body unit 120 includes a bottom surface part, and a wall surface part is formed at one end of a side of the bottom surface part. At least a part of the opposite side of the wall surface part is open for thereby forming a space "A" through which the driving roller 140 to pass, along with the opened portion of the first body unit 110. In the wall surface part of the second body unit 120, grooves may be also formed where fingers contact in order to grab with hands.

The first body unit 110 and the second body unit 120 may be secured to each other in a variety of ways. For example, there may be provided a configuration wherein the first body unit 110 may have a pillar with a hook, and a groove into which the hook may be snapped is formed at a corresponding portion of the second body unit. In addition, it is possible to provide a configuration wherein four engaging members may formed at either the first body unit 110 or the second body unit 120, and screw may be inserted into the remaining one for thereby engaging both the first body unit 110 and the second body unit 120. In addition, two engaging members may be formed an end portion of one side in the longitudinal direction of either the first body unit 110 or the second body unit 120, and two engaging members may be formed at an end portion of the other side of the remaining one of both the body units. In this way, the engagement of the first body unit 110 and the second body unit 120 may be performed in many various ways. The present invention is not limited to a specific engaging method.

The IV flow tube passes in the longitudinal direction through the space formed inside by means of the first body unit 110 and the second body unit 120. For this operation, a space through which the IV flow tube passes is formed between the first body unit 110 and the second body unit 120.

The fixed roller 130 is accommodated in the fixed roller accommodation space formed between the first body unit 110 and the second body unit 120. Both ends of a shaft 135 of the fixed roller 130 are inserted into the fixed roller grooves 115 formed at the first body unit 110 and the second body unit 120, so that the fixed roller 130 may be rotatably and fixed at both the first and second body units 110 and 120.

Figure 11:
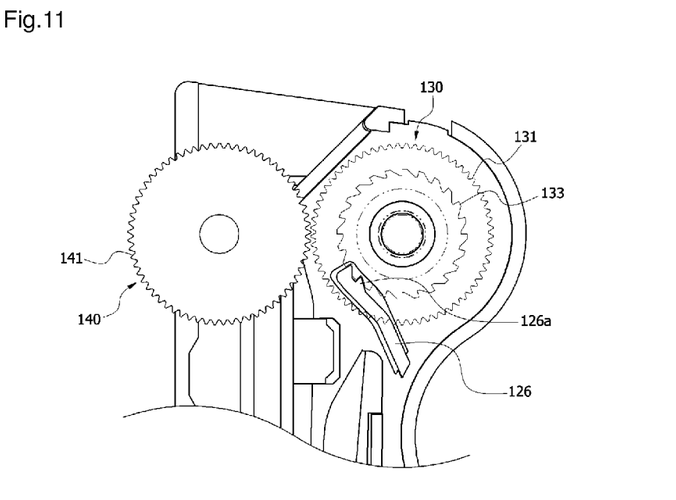
FIG. 11 is a view for describing a reverse rotation prevention structure for preventing an operation where a flushing function is performed in the reverse direction.
Figure 12:
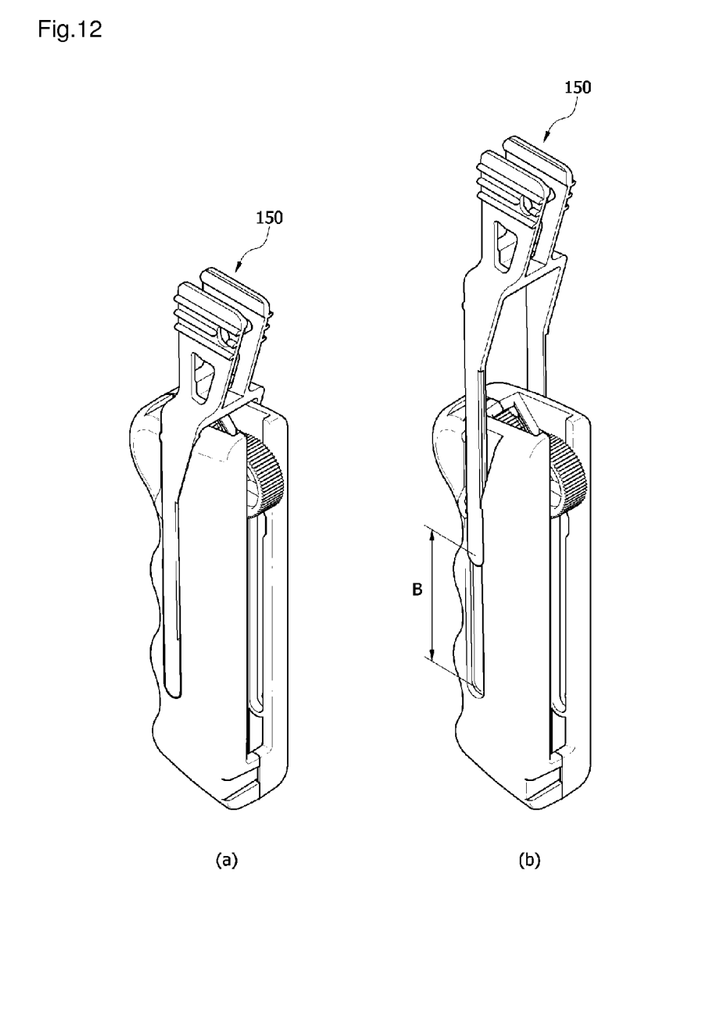
FIG. 12 is a view for describing an operational principle of a clip for limiting a range of flushing operations.

The fixed roller 130 is formed of a double-layered gear of a first gear unit 131 and a second gear unit 133. As illustrated in FIG. 11, the first gear unit 131 is engaged with a gear unit 141 formed at the driving roller 140 and rotates the fixed roller 130 together with the driving roller 140 in the course of the flushing operation. The second gear unit 133 is formed of a ratchet gear and serves to prevent the reverse rotation by means of a pawl provided at an inner side of the second body unit 120. Since a protrusion portion 126a of the pawl 126 engaged with the gear of the second gear unit 133 allows only the rotation in one direction, as illustrated in FIG. 12, the fixed roller 130 is formed in a structure wherein it may rotate in the clockwise direction, but does not rotate in the counterclockwise direction. In addition, since the pawl 126 has an elastic force, a snapping-like feeling may be obtained when the pawl 126 shifts to the next gear after the pawl 126 is engaged with one gear of the second gear unit 133 as the fixed roller 130 rotates.

The driving roller 140 may be accommodated between the first body unit 110 and the second body unit 120, with part of the driving roller 140 being exposed toward the opened space "A". The user may regulate the position of the driving roller 140 by rotating the exposed portion. More specifically, the flow of IV solution may be regulated since the degree where the IV flow tube is pressed against the tube pressing surfaces 113 and 123 while the driving roller 140 moves along the longitudinal directions of the first body unit 110 and the second body unit 120.

In order to move the driving roller 140 between the first body unit 110 and the second body unit 120, a first driving roller guide groove is formed at one surface facing the second body unit 120 of the bottom surface part of the first body unit 110 so as to guide the driving roller 140 in the longitudinal direction while accommodating the end portion of one side of the shaft 145 of the driving roller 140. In addition, a second driving roller guide groove is formed at a portion corresponding to the first driving roller guide groove of the second body unit 120 so as to guide the driving roller 140 in the longitudinal direction. Hereinafter, the first driving roller guide groove and the second driving roller guide groove are collectively called a driving roller guide groove.

Meanwhile, in order to vary the degree where the IV flow tube is pressed against the tube pressing surfaces 113 and 123 while the driving roller 140 moves along the longitudinal directions of the first body unit 110 and the second body unit 120, at least a part of each of the tube pressing surfaces 113 and 123 is preferably formed in a shape of a slanted surface. In addition, it may be constituted that the distance between the tube pressing surfaces 113 and 123 and the driving roller guide groove gradually varies while the driving roller 140 moves along the longitudinal direction.

Figure 5:
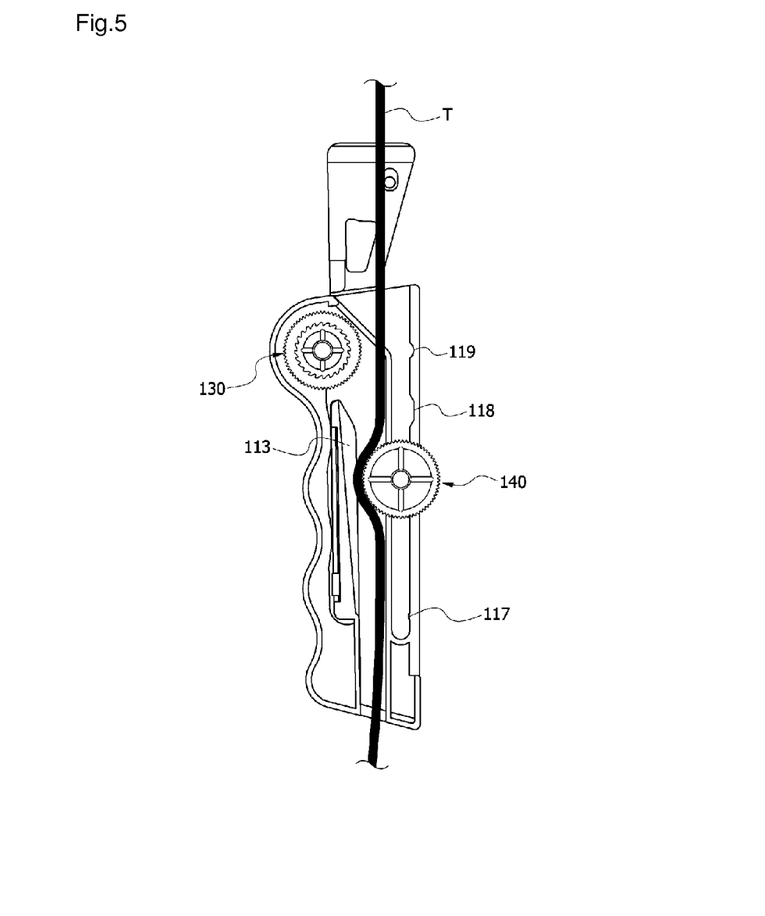
FIG. 5 is a cross sectional view for describing an IV flow control mechanism of an IV flow controller according to the present invention.

As illustrated in FIG. 5, the driving roller 140 may move in the longitudinal direction along the driving roller guide groove. In the driving roller guide groove, there are formed a flushing escape groove 119, an escape groove 118, and a protrusion 117 which provides a snapping-like feeling in order to inform that it enters where the IV solution does not flow through the IV flow tube "T". The above configuration will be described in detail with reference to FIGS. 6 to 10.

Figure 6:
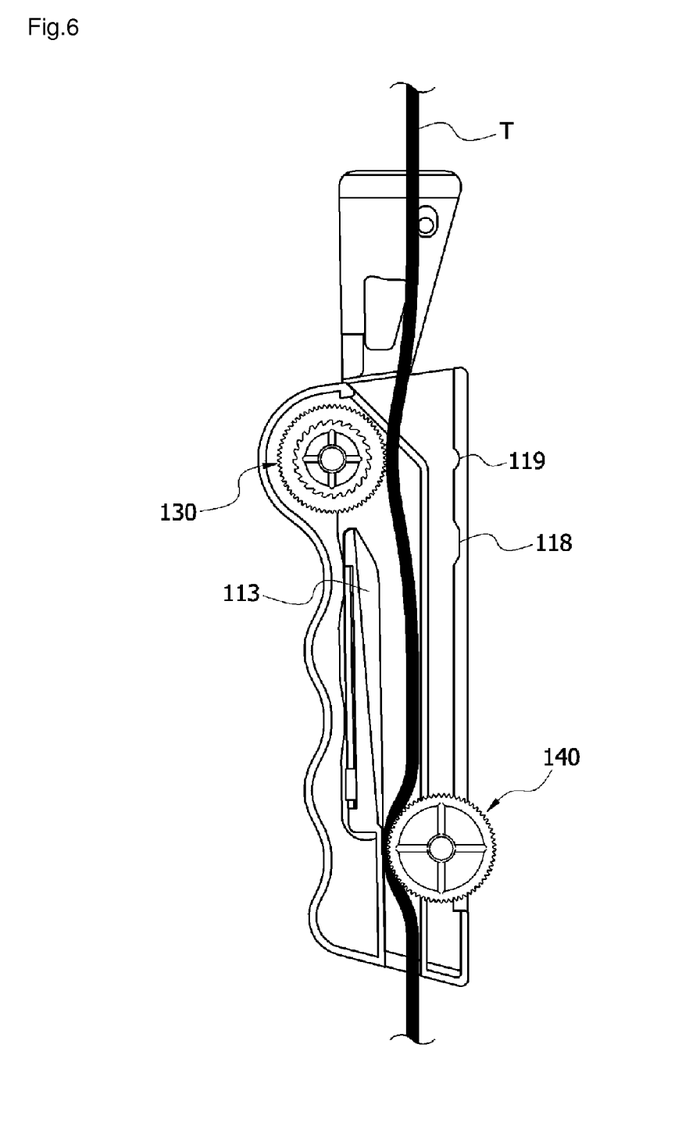
FIGS. 6 to 10 are cross sectional views illustrating the position of a driving roller during the IV flow control and flushing operation of an IV flow controller according to the present invention.
Figure 7:
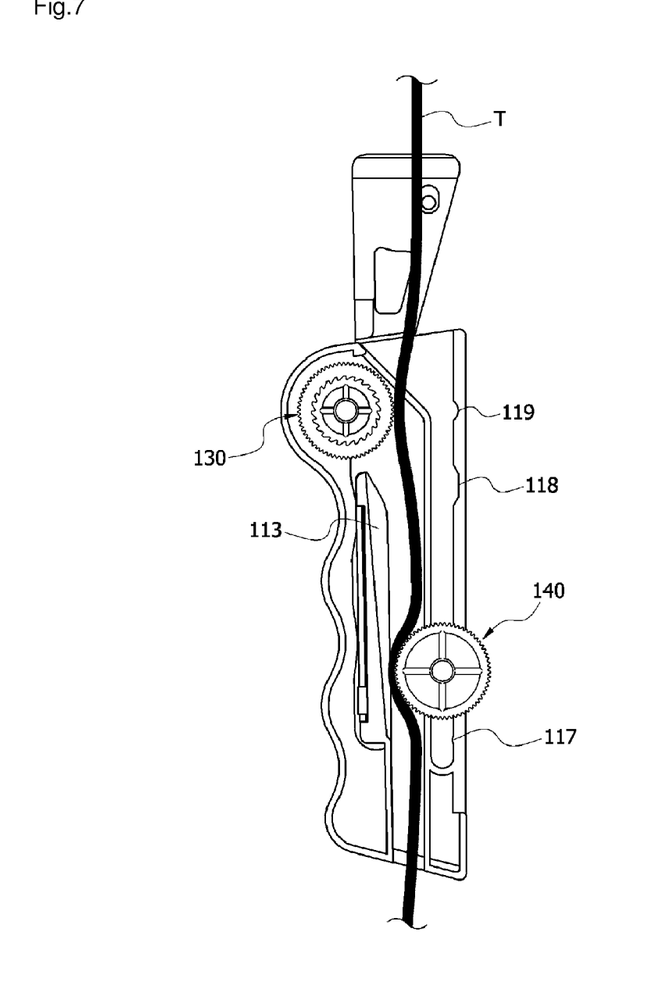
Figure 8:
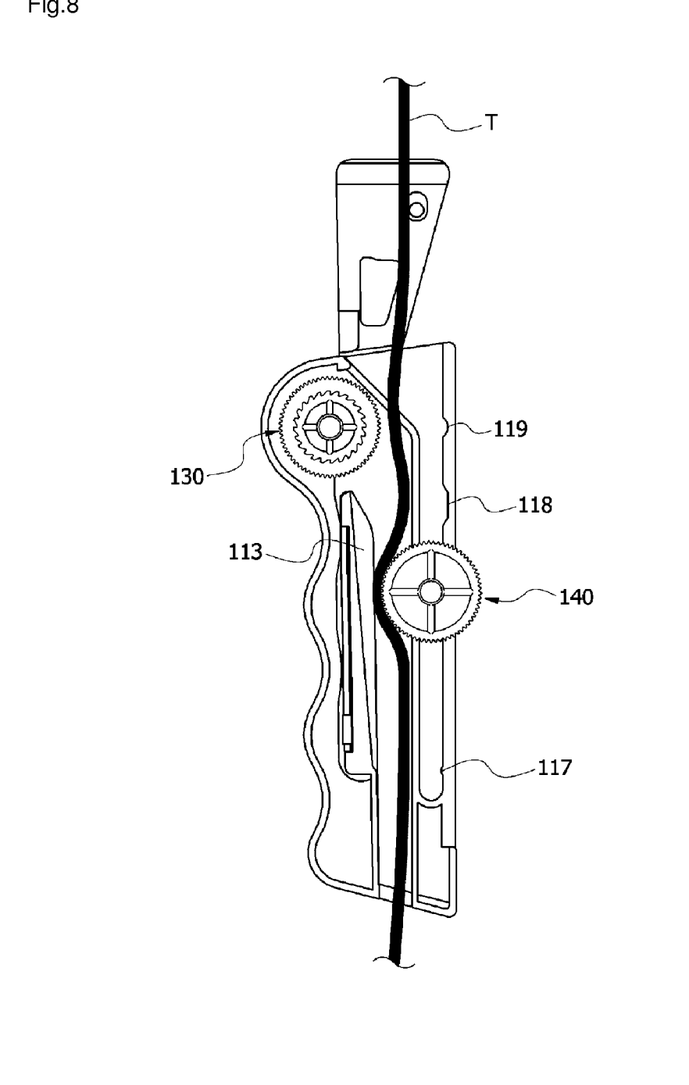

The procedures for regulating the rate of the IV solution flowing through the IV flow tube "T" based on the position of the driving roller 140 are illustrated in FIGS. 6 to 8.

FIG. 6 illustrates a state where the driving roller 140 is positioned at a portion where the IV solution does not flow through the IV flow tube "T". At the above position (IV flow-blocking position), a tube pressing surface 113 is formed at a distance where the IV solution does not flow through the IV flow tube since the driving roller 140 maximally presses the IV flow tube "T". It is preferred that the tube pressing surface is characterized in that different from the other portions, the contacting surface with the driving roller 140 is a plane, not the slanted surface.

FIG. 7 illustrates a state where the driving roller 140 is positioned where an IV solution flows a little through the IV flow tube "T", deviating from the position in FIG. 6. Since the protrusion 117 is formed at the driving roller guide groove near the IV flow-blocking position, the user may feel a snapping-like feeling with the aid of the protrusion 117 when the driving roller 140 deviates from the IV flow-blocking position. The tube pressing surface 113 is formed in a shape of the slanted surface. In other words, as illustrated in FIGS. 6 to 10, the left portion of the tube pressing surface 113 is higher than the right portion thereof. Therefore, at the position in FIG. 7, since the tube pressing surface 113 is closer to the driving roller 140 than the position in FIG. 8, the IV flow tube "T" may be more pressed by means of the driving roller 140. Therefore, the amount of the flowing IV solution in FIG. 7 is smaller than that in FIG. 8. Meanwhile, FIGS. 6 to 10 illustrate only the inner surface of the first body unit 110, however since the inner surface of the second body unit 120 has the same configuration, the IV flow tube "T" may be pressed between the driving roller 140 and the tube pressing surfaces 113 and 123.

Figure 9:
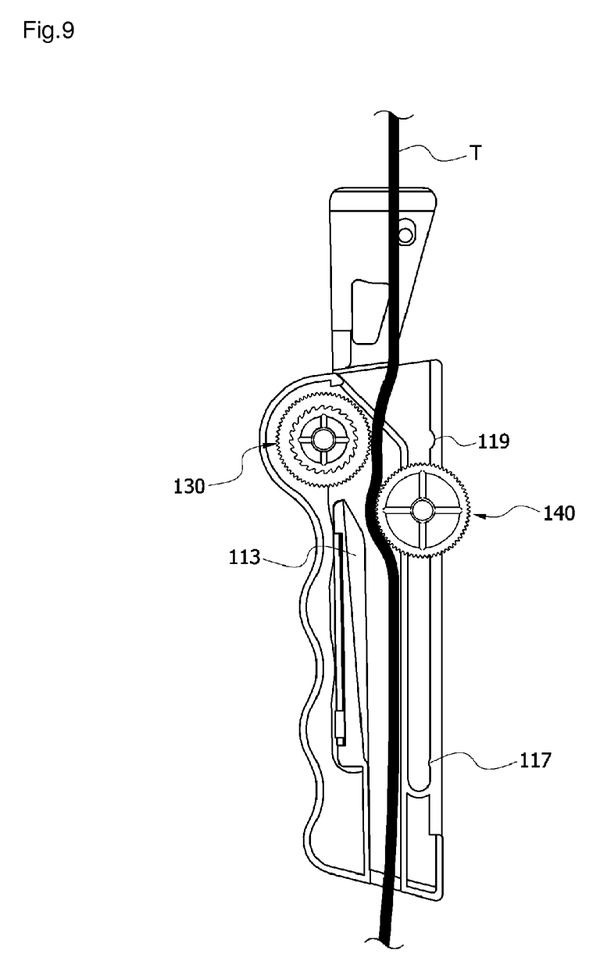

The escape groove 118 may be formed almost in front of an end portion of one side of the driving roller guide groove. As illustrated in FIG. 9, when the driving roller 140 reaches the position of the escape groove 118, the driving roller 140 enters into the escape groove 118 while generating a snapping-like feeling and at the same time becomes a state where the pressure is never applied to the IV flow tube "T" or if any, minimally applied.

Figure 10:
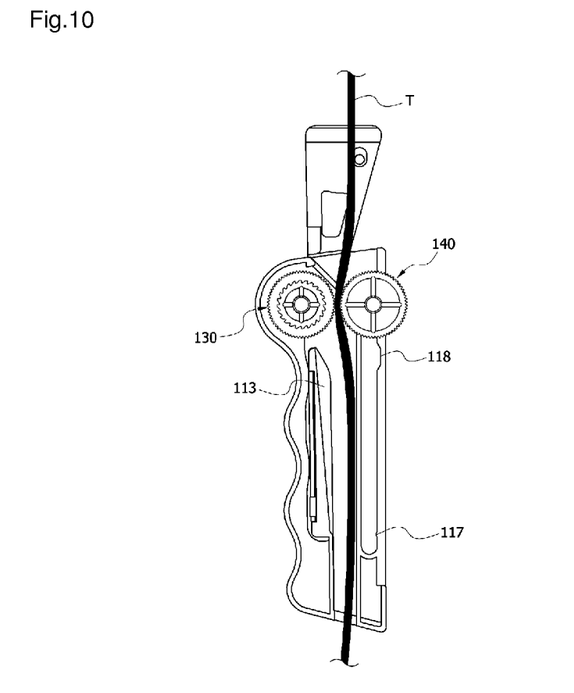

The flushing may be performed by moving the driving roller 140 past the escape groove 118 and to where the fixed roller 130 would face (flushing position), the operational state of which is illustrated in FIG. 10. At this position, the gear unit 141 of the driving roller 140 is engaged with the first gear unit 131 of the fixed roller 130 with the IV flow tube "T" being disposed between them, so the driving roller 140 rotates in cooperation with the fixed roller 130. Therefore, in this state, the IV flow controller 100 is dragged down, the flushing operation is performed. As described with reference to FIG. 11, in the course of the flushing operation, the snapping-like feeling may be enhanced since the protrusion portion 126a of the pawl 126 is repeatedly engaged with or disengaged from the gear unit while the second gear unit 133 of the fixed roller 130 rotates.

Meanwhile, as illustrated in FIGS. 6 to 10, it is preferred that the flushing escape groove 119 is formed at the flushing position of the driving roller guide groove. The user may easily recognize when the driving roller 140 enters the flushing position with the aid of the snapping-like feeling which generates when it inters into the flushing escape groove 119, and it is possible to the driving roller 140 from separating from the flushing position in the middle of the flushing operation.

Next, the configuration for limiting the flushing operation range by means of the clip 150 will be described with reference to FIGS. 1, 2 and 12.

The clip 150 includes leg units 151a and 151b and handle units 153a and 153b. Engaging hooks 152a and 152b are formed inside of the end of leg units 151a and 151b. Engaging hooks 152a and 152b are inserted into the slits 121a and 111a which formed at second body unit 120 and first body unit 110. Leg unit 151a and 151b is also accommodated in clip accommodation grooves 111 and 121.

In the handle units 153a and 153b of the clip 150, a groove 155 is formed at one side of each of the handle units, and a protrusion 156 is formed at the other side of each of the handle units, so that the clip 150 may be fixed at the IV flow tube "T" by inserting the protrusion 156 into the groove 155.

When the IV flow controller body is pushed down for the sake of flushing in a state in FIG. 12A after the clip 150 is fixed at the IV flow tube "T", since the clip 150 is fixed at the IV flow tube "T", only the IV flow controller body moves down, and the engaging hooks 152a and 152b of the clip 150 becomes a state where it is relatively moved upward along slits 111a and 121a with respect to the IV flow controller body, more specifically, it becomes a state where it relatively has moved downward with respect to the clip 150 to which the IV flow controller body is fixed (the state in FIG. 12B). At this time, when the engaging hooks 152a and 152b of the clip 150 come into contact with the end portions of the tops of each of the slits 111a and 121a, since the IV flow controller body no longer moves downward, the operational range of the IV flow controller may be limited to the range indicated by the letter "B" in FIG. 12 at the time of flushing.

The present invention has been descried along with examples. Just because all the components belonging to the exemplary embodiments of the present invention have been combined into one or have been configured to operate in a combined form, the present invention should not be interpreted to be limited by such exemplary embodiments. In other words, one or more than one of such components may be selectively combined and may be configured to operate within the scope of the present invention. In addition, it is obvious that each of such components may be substituted with a component which has the same function.

The terms "comprise", "includes", "has", etc. used represents unless otherwise stated that a corresponding component may be included, so it should be interpreted to include another component, not excluding the component.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

We claim:

1. An IV flow controller having a flushing feature, comprising:
   a first body unit which includes a bottom surface part and a wall surface part, with an open space being formed at the opposite side of the wall surface part, the first body unit further including a tube pressing surface and a fixed roller groove;
   a second body unit which is secured to the first body unit and forms a space through which an IV flow tube passes, in a longitudinal direction between the second body unit and the first body unit, the second body unit including a tube pressing surface and a fixed roller groove;
   a fixed roller which is rotatably fixed since a shaft is inserted in the fixed roller groove of each of the first body unit and the second body unit and includes a first gear unit, and a second gear unit formed of a latchet gear; and
   a driving roller which is configured in such a way that part of the driving roller is accommodated between the first body unit and the second body unit, while being exposed toward the open space, and when the exposed portion is rotated, the flow of the IV solution is regulated since the degree when an IV flow tube is pressed against the tube pressing surface varies while moving along the longitudinal directions of the first body unit and the second body unit, and the flushing is performed at a flushing position of an end portion of one side moving along the longitudinal direction since the driving roller rotates in cooperation with the first gear unit of the fixed roller with the IV flow tube being disposed between the first gear unit and the driving roller, wherein the second body unit includes a pawl which is engaged with the latchet gear for thereby preventing reverse rotation.

2. The controller of claim 1, wherein a first driving roller guide groove is formed at the bottom surface part of the first body unit so as to accommodate an end portion of one side of the shaft of the driving roller and to guide the driving roller in the longitudinal direction, and a second driving roller guide groove is formed at a portion corresponding to the first driving roller guide groove of the second body unit so as to guide the driving roller in the longitudinal direction.

3. The controller of claim 2, wherein at least a part of the tube pressing surface is formed of a slanted surface, and the average distance between the tube pressing surface and the first and second driving roller guide grooves gradually varies while the driving roller moves along the longitudinal direction.

4. The controller of claim 2, wherein in the first driving roller guide groove and the second driving roller guide groove, since an escape groove is formed near the position of the end portion of one side moving along the longitudinal direction and toward the open space, when the driving roller enters into the escape groove, the pressing of the IV flow tube between the driving roller and the wall surface unit is minimized.

5. The controller of claim 2, wherein a flushing escape groove is formed at each of the first and second driving roller guide grooves of the flushing position.

6. An IV flow controller having a flushing feature, comprising:
   a first body unit which includes a bottom surface part and a wall surface part, with an open space being formed at the opposite side of the wall surface part, the first body unit further including a tube pressing surface and a fixed roller groove;
   a second body unit which is secured to the first body unit and forms a space through which an IV flow tube passes, in a longitudinal direction between the second body unit and the first body unit, the second body unit including a tube pressing surface and a fixed roller groove;

a fixed roller which is rotatably fixed since a shaft is inserted in the fixed roller groove of each of the first body unit and the second body unit and includes a first gear unit and a second gear unit; and a driving roller which is configured in such a way that part of the driving roller is accommodated between the first body unit and the second body unit, while being exposed toward the open space, and when the exposed portion is rotated, the flow of the IV solution is regulated since the degree when an IV flow tube is pressed against the tube pressing surface varies while moving along the longitudinal directions of the first body unit and the second body unit, and the flushing is performed at a flushing position of an end portion of one side moving along the longitudinal direction since the driving roller rotates in cooperation with the first gear unit of the fixed roller with the IV flow tube being disposed between the first gear unit and the driving roller, wherein a first driving roller guide groove is formed at the bottom surface part of the first body unit so as to accommodate an end portion of one side of the shaft of the driving roller and to guide the driving roller in the longitudinal direction, and a second driving roller guide groove is formed at a portion corresponding to the first driving roller guide groove of the second body unit so as to guide the driving roller in the longitudinal direction, and a tube pressing surface is formed at a distance where the flowing of the IV solution through the IV flow tube is blocked since the driving roller maximally presses the IV flow tube at the IV flow-blocking position at the end portion of the opposite side of the flushing position, and a protrusion is formed at each of the first and second driving guide roller grooves formed near the IV flow-blocking position so as to obtain a snapping-like feeling.

7. The controller of claim 6, wherein the second gear unit of the fixed roller is a latchet gear, and the second body unit includes a pawl which is engaged with the latchet gear for thereby preventing reverse rotation.

8. An IV flow controller having a flushing feature, comprising:

a first body unit which includes a bottom surface part and a wall surface part, with an open space being formed at the opposite side of the wall surface part, the first body unit further including a tube pressing surface and a fixed roller groove;

a second body unit which is secured to the first body unit and forms a space through which an IV flow tube passes, in a longitudinal direction between the second body unit and the first body unit, the second body unit including a tube pressing surface and a fixed roller groove;

a fixed roller which is rotatably fixed since a shaft is inserted in the fixed roller groove of each of the first body unit and the second body unit and includes a first gear unit and a second gear unit; and a driving roller which is configured in such a way that part of the driving roller is accommodated between the first body unit and the second body unit, while being exposed toward the open space, and when the exposed portion is rotated, the flow of the IV solution is regulated since the degree when an IV flow tube is pressed against the tube pressing surface varies while moving along the longitudinal directions of the first body unit and the second body unit, and the flushing is performed at a flushing position of an end portion of one side moving along the longitudinal direction since the driving roller rotates in cooperation with the first gear unit of the fixed roller with the IV flow tube being disposed between the first gear unit and the driving roller, and the IV flow controller includes two leg units at each of which an engaging hook is formed inside, and a clip having two handle units, and a clip accommodation groove is formed at an outer surface of each of the first body unit and the second body unit for thereby accommodating the clip, and a slip in which the engaging hook is inserted and is movable is inserted in the clip accommodation groove.

9. The controller of claim 8, wherein a groove is formed at one side of the handle unit of the clip, and a protrusion which is inserted into the groove is formed at the other side of the handle unit.

10. The controller of claim 8, wherein the second gear unit of the fixed roller is a latchet gear, and the second body unit includes a pawl which is engaged with the latchet gear and is configured to prevent reverse rotation.

* * * * *